US006500410B1

(12) United States Patent
Griesbach et al.

(10) Patent No.: US 6,500,410 B1
(45) Date of Patent: Dec. 31, 2002

(54) SUN PROTECTION AGENTS

(75) Inventors: Ute Griesbach, Dusseldorf (DE); Rolf Wachter, Dusseldorf (DE); Bernd Fabry, Korschenbroich (DE); Michael Heyer, Erkrath (DE); Rolf E. Engstad, Tromso (NO)

(73) Assignee: Biotec Pharmacon ASA, Tromso (NO)

( * ) Notice: Subject to any disclaimer, the term of this patent is extended or adjusted under 35 U.S.C. 154(b) by 0 days.

(21) Appl. No.: 09/937,013

(22) PCT Filed: Mar. 3, 2000

(86) PCT No.: PCT/EP00/01835

§ 371 (c)(1),
(2), (4) Date: Jan. 25, 2002

(87) PCT Pub. No.: WO00/54734

PCT Pub. Date: Sep. 21, 2000

(30) Foreign Application Priority Data

Mar. 12, 1999 (DE) .......................................... 199 11 052

(51) Int. Cl.$^7$ ............................. A61K 7/42; A61K 7/00; A61K 35/78; A61K 31/715; A01N 25/00
(52) U.S. Cl. ........................... 424/59; 424/60; 424/400; 424/401; 424/404; 424/405; 424/195.16; 514/54
(58) Field of Search ............................ 424/59, 60, 400, 424/401, 195.16, 405, 404; 514/54

(56) References Cited

U.S. PATENT DOCUMENTS 5,397,773 A    3/1995    Donzis

FOREIGN PATENT DOCUMENTS

| EP | 0681830 | 11/1995 |
| EP | 0875244 | 11/1998 |
| WO | WO9530022 | 11/1995 |

*Primary Examiner*—Shelley A. Dodson
(74) *Attorney, Agent, or Firm*—Ladas & Parry

(57) ABSTRACT

The invention relates to sun-protection agents containing (a) water soluble β-(1,3) glucans that are substantially devoid of β-(1,6) links, and (b) UV sun-protection factors.

10 Claims, No Drawings

SUN PROTECTION AGENTS

FIELD OF THE INVENTION

The invention relates to the field of sun cosmetics and concerns to novel preparations with a content of specific glucans and UV light protection factors as well as the use of the glucans for improvement of the photosensitivity of the light protection factors.

PRIOR ART

The cosmetic sun protection products protect the human skin not only against the direct results of UV-A and UV-B radiation, i.e. against sunburn, but also against the indirect results in the form of skin aging and skin cancer. Therefore normally organic filtering substances are used, which because of their chemical structure are able to absorb ultraviolet light. Through the uptake of the UV-radiation electrons in the filter molecule are brought into an excited state. The energy which thereby is taken up is thereafter again set free as radiation of heat, whereby photosensitive molecules are going back into their energetic ground state, whereas in the case of photoinsensitive filters, to which the bigger part of the known light protection factors belong, a chemical change occurs, such as e.g. an isomerization or a radical degradation. In addition to the not always satisfactory photostability of the light protection factors, another problem resists in that the filters—also in cosmetic oils—only have a limited solubility, respectively dispersing ability. Thereby it can happen that the substances during storage precipitate or sediment, whereby the light protection preparation looses a substantial part of its efficiency.

In this connection reference is made to the European patent EP-B1 0500718 (Donzis), from which the use of glucans in sun protecting agents is known. The glucans are obtained through extraction from the cell walls of yeasts, they are insoluble in water and contain (1,6) linkages. Further in EP-A1 0681830 (Unilever) sun protection agents are suggested which contain ethylene/vinyl acetate copolymers and polyacrylates, UV light protection filters and possibly also up to 10% by weight of glucans.

Therefore the task of the present invention was to improve both the oil solubility and the oil dispersability of UV light protection factors, and also their photosensitivity. Further preparations should be made available which compared to the products according to known art should be distinguished through immune modulating or immune stimulating properties, improved adhesion, film forming abilities and water resistance.

DESCRIPTION OF THE INVENTION

The object of the invention is sun protection agents, containing (a) water soluble β-(1,3) glucans, substantially free from β-(1,6)-bonds, and (b) UV light protection factors.

Surprisingly it was found that the addition of β-(1,3) glucans, which are substantially free from β-(1,6) linkages not only increase the solubility or dispersability of UV light protection factors in cosmetic oils, but also vitally improve their photosensitivity, whilst glucans, which are insoluble in water, and which have noteworthy contents of β-(1,6) links, show no effect both in direction of solubilisation and in direction of photosensitivity. The invention comprises the perception that the agents stimulate the immune system and have an improved adhesion, film formation and water resistance.

Water Soluble β-(1,3) Glucans

The term glucans is intended to mean homopolysaccharides based on glucose. Depending on sterical linking there is a difference between β-(1,3), β-(1,4) and β-(1,6) glucans. β-(1,3) Glucans normally show a helical structure, whereas glucans with a (1,4) linkage generally have a linear structure. The β-glucans of the invention have a (1,3) structure, i.e. they are substantially free from undesired (1,6) linkages. Preferably such β-(1,3) glucans are used where the side chains exclusively show (1,3) linkages. Especially the agents contain glucans which are obtained on the basis of yeast from the family Sacchaomyces, especially *Saccharomyces cerevisiae*. Glucans of this type are available in technical amounts according to known methods. The international patent application WO 95/30022 (Biotec-Mackzymal) describes e.g. a method for producing such substances, wherein glucans with β-(1,3) and β-(1,6) linkages are brought in contact with β-(1,6) glucanases in such a way, that practically all β-(1,6) linkages are loosened. Preferably used for the manufacture of these glucans are glucanases based on *Trichodermia harzianum*. As to the manufacture and availability of the glucans contained in these agents, reference is made to the above cited publication.

UV Light Protection Factors

UV light protection factors are e.g organic substances (light protection filters) which by room temperature are in liquid or crystalline form, and which are capable of absorbing ultraviolet radiation and to give free the received energy in the form of radiation with long wavelength, e.g. in the form of heat. UVB filters can be soluble in oils or in water. As oil soluble substances the following are mentioned as examples:

3-Benzyliden camphor, respectively 3-benzylidene norcamphor and the derivatives thereof, e.g. 3-(4-methylbenzylidene) camphor as described in EP-B1 0693471;

4-aminobenzoic acid derivatives, preferably 4-(dimethylamino) benzoic acid 2-ethylhexylester, 4-(dimethylamino) benzoic acid 2-octylester and 4-(dimethylamino) benzoic acid amylester;

esters of cinnamonic acid, preferably 4-methoxy cinnamoic acid 2-ethylhexylester, 4-methoxy cinnamoic acid propylester, 4-methoxy cinnamoic acid isoamylester, 2-cyano-3,3-phenyl cinnamoic acid 2-ethythexylester (octocrylene);

esters of salicylic acid, preferably salicylic acid 2-ethylhexylester, salicylic acid 4-isopropyl benzylester, salicylic acid homomenthylester;

derivatives of benzophenone, preferably 2-hydroxy-4-methoxy benzophenone, 2-hydroxy-4-methoxy-4'-methyl benzophenone, 2,2'-dihydroxy-4-methoxy benzophenone;

esters of benzalmalonic acid, preferably 4-methoxy benzmalonic acid 2-ethylhexyl ester, triazine derivatives, such as e.g. 2,4,6-trianilino-(p-carbo-2'-ethyl-1'-hexyloxy)-1,3,5-triazine and octyltriazone, as described in EP A1 0818450;

propane-1,3-diones, such as e.g. 1-(4-tert.-butylphenyl)-3-(4'-methoxyphenyl)-propane-1,3-dion;

ketotricyclo(5,2,1,0)-decane derivatives, as described in EP-B1 06945521.

As water soluble substances can be mentioned:

2-Phenylbenzimidazol-5-sulfonic acid and the alkali, aalkaline earth, ammonium, alkylammonium, alkanolammonium and glucammonium salts;

sulfonic acid derivatives of benzophenones, preferably 2-hydroxy-4-methoxybenzophenon-5-suflfonic acid and their salts;

sulfonic acid derivatives of 3-benzylidencamphen, such as e.g. 4-(2-oxo-3-bornylidenmethyl)-benzolsulfonicc acid and 2-methyl-5-(2-oxo-bornyliden)-sulfonic acid and their salts.

As typical UV-A filter especially derivatives of benzoyl methane comes in question, such as e.g. 1-(4'-tert.-butylphenyl)-3-(4'-methoxyphenyl)propane-1,3-dion, 4-tert.butyl-4'-methoxydibenzoyl-methan (Parsol 1789), or 1-phenyl-3-(4'-isopropylphenyl-propane-1,3-dion. The UV-A and UV-B filters of course also can be used in mixtures. In this case combinations of octocrylene or camphor derivatives with butyl methoxydibenzoylmethane are especially photosensitive.

In addition to the mentioned soluble substances also insoluble light protection pigments can be used for this purpose, i.e. fine disperse metal oxides or salts. Examples of suitable metal oxides are especially zinc oxide and titanium dioxide and in addition other oxides of iron, zirconium, silicon, manganese, aluminium and cerium, as well as their mixtures. As salts silicates (talk), barium sulphate or zinc stearate can be used. The oxides and salts are used in form of the pigments for skin caring and skin protecting emulsions and decorative cosmetics. The particles should have an average diameter of less than 100 nm, preferably between 5 and 50 nm and especially between 15 and 30 nm. They can have a spherical shape, but particles can also be used which have an ellipsoidal form or else have a shape which differs from the spherical shape. In sun protecting agents preferably so-called micro or nano pigments are used. Preferably micronized zinc oxide is used.

Further suitable UV light protection factors can be found in the survey by P. Finkel in SÖSFW-Journal 122, 543 (1996). Likewise suitable are herbal extracts with UV absorbing or antioxidative properties. In a preferable version of the invention the agents contain (a) 0.01 to 25, preferably 0.5 to 15 and especially 1 to 5% by weight of water soluble β-(1,3) glucans, which are substantially free from β-(1,6) linkages, and (b) 0.05 to 10, preferably 0.5 to 8 and especially 1 to 5% by weight of UV light protection factors, provided that the stated amounts are filled up to 100% by weight with water as well as where appropriate further auxiliary and additional substances.

Commercial Applicability

The addition of β-(1,3) glucans, which are substantially free from β-(1,6) linkages, not only improves the solubility or dispersability of UV light protection factors in cosmetic oils, but also increase their photosensitivity. Another object of the invention is therefore the use of the mentioned substances for improvement of the photostability and solubility of UV light protection factors in sun protecting agents.

Sun Protection Agents

The sun protection agents according to the invention, such as for example cremes, lotions, oils, gels, sticks and suchlike, can further as additional auxiliary and additional agents contain mild surfactants, oil bodies, emulsifiers, hyperfatting agents, pearl lustre waxes, consistency substances, thickening agents, polymers, silicone compounds, fats, waxes, stabilizing agents, biogenic active substances, deodorants, agents against dandruff, film forming agents, swelling agents, antioxidants, inorganic color pigments, hydrotropes, preservatives, insect repellents, self tanning agents, solubilizing agents, perfume oils, colouring agents and suchlike.

Typical examples of suitable mild, i.e. especially skin compatible surfactants are fatty alcohol polyglycol ether sulphates, monoglyceride sulphates, mono- and/or dialkyl sulfosuccinates, fatty acid isethionates, fatty acid sarcosinates, fatty acid taurides, fatty acid glutamates, α-olefin sulphonates, ethercarboxylic acids, alkyl oligoglucosides, fatty acid glucamides, alkylamido betaines and/or protein fatty acid condensates, the last mentioned preferably based on wheat proteins.

As oil bodies use can be made of for example Guerbet alcohols based on fatty alcohols with 6 to 18, preferably 8 to 10 carbon atoms, esters of linear $C_6-C_{22}$ fatty acids with linear $C_6-C_{22}$ fatty alcohols, esters of branched $C_6-C_{13}$ carboxylic acids with linear $C_6-C_{22}$ fatty alcohols, such as e.g. myristyl myristate, myristyl palmitate, myristyl stearate, myristyl isostearate, myristyl oleate, myristyl behenate, myristyl erucate, cetyl myristate, cetyl palmitate, cetyl stearate, cetyl isostearate, cetyl oleate, cetyl behenate, cetyl erucate, stearyl myristate, stearyl palmitate, stearyl stearate, stearyl isostearate, stearyl oleate, stearyl behenate, stearyl erucate, isostearyl myristate, isostearyl palmitate, isostearyl stearate, isostearyl isostearate, isostearyl oleate, isosteayl behenate, isostearyl oleate, oleyl myristate, oleyl palmitate, oleyl stearate, oleyl isostearate, oleyl oleate, oleyl behenate, oleyl erucate, behenyl myristate, behenyl palmitate, behenyl stearate, behenyl isostearate, behenyl oleate, behenyl behenate, behenyl erucate, erucyl myristate, erucyl palmitate, erucyl stearate, erucyl isostearate, erucyl oleate, erucyl behenate and erucyl erucate. In additon esters of linear $C_6-C_{22}$ fatty acids with branched alcohols, especially 2-ethylhexanol, esters of hydroxycarboxylic acids with linear or branched $C_6-C_{22}$ fatty alcohols, especially dioctyl malate, esters of linear and/or branched fatty acids with polyvalent alcohols (such as e.g. propylene glycol, dimeric diol or trimeric triol) and/or Guerbet alcohols, triglycerides based on $C_6-C_{10}$ fatty acids, liquid mixtures of mono-/di-/triglycerides based on $C_6-C_{18}$ fatty acids, esters of $C_6-C_{22}$ fatty alcohols and/or Guerbet alcohols with aromatic carboxylic acids, especially benzoic acid, esters of $C_2-C_{12}$ dicarboxylic acids with linear or branched alcohols with 1 to 22 carbon atoms or polyols with 2 to 10 carbon atoms and 2 to 6 hydroxyl groups, plant oils, branched primary alcohols, substituted cyclohexanes, linear and branched $C_6-C_{22}$ fatty alcohol carbonates, Guerbet carbonates, esters of benzoic acid with linear and/or branched $C_6-C_{22}$ alcohols (e.g. Finsolv® TN), linear or branched, symmetrical or unsymmetrical dialkyl ethers with 6 to 22 carbon atoms in each alkyl group, ring opening products of epoxydated fatty acid esters with polyols, silicone oils and/or aliphatic or naphthenic hydrocarbons, such as e.g. squalan, squalen or dialkyl cyclohexanes, can be used As emulsifiers for example nonionic surfactants from at least one of the following groups may be used:

(1) Addition products of 2 to 30 moles ethylene oxide and/or 0 to 5 moles propylene oxide on linear fatty alcohols with 8 to 22 C atoms, on fatty acids with 12 to 22 C atoms and on alkyl phenols with 8 to 15 C atoms in the alkyl group;

(2) $C_{12/18}$ fatty acid mono- and -diesters of addition products of 1 to 30 moles ethylene oxide and glycerol;

(3) glycerol mono- and diesters and sorbitan mono- and diesters of saturated and unsaturated fatty acids with 6 to 22 carbon atoms and their ethylene oxide addition products;

(4) alkyl mono- and oligoglycosides with 8 to 22 carbon atoms in the alkyl group and their ethoxylated analogues;

(5) addition products of 15 to 60 moles ethylene oxide on ricinus oil and/or hardened ricinus oil;

(6) polyol and especially polyglycerol esters, such as e.g. polyglycerol polyricinoleate, polyglycerol poly-12- hydroxystearate or polyglycerol dimerate isostearate, and also mixtures of compounds from more of these classes of substances;

(7) addition products of 2 to 15 moles ethylene oxide on ricinus oil and/or hardened ricinus oil;

(8) partial esters based on linear, branched, unsaturated or saturated $C_{6/22}$ fatty acids, ricinolic acid and 12-hydroxy stearic acid and glycerol, polyglycerol, pentaerythrite, dipentaerythrite, sugar alcohols (e.g. sorbitol), alkyl glucosides (e.g. methyl glucoside, butyl glucoside, lauryl glucoside) as well as polyglucosides (e.g. cellulose);

(9) mono-, di- and trialkylphosphates as well as mono-, di- and/or tri-PEG alkylphosphates and their salts;

(10) wool wax alcohols;

(11) polysiloxane/polyalkyl/polyether copolymers or corresponding derivatives;

(12) mixed esters of pentaerythrite, fatty acids, citric acid and fatty alcohol according to DE 1165574 PS and/or mixed esters of fatty acids with 6 to 22 carbon atoms, methyl glucose and polyols, preferably glycerol or polyglycerol,

(13) polyalkylene glycols, as well as

(14) glycerol carbonate.

The addition products of ethylene oxide and/or of propylene oxide on fatty alcohols, fatty acids, alkyl phenols, glycerol mono- and diesters as well as sorbitan mono- and -diesters of fatty acids or on ricinus oil are known products which are commercially available. They are mixtures of homologous substances, with average degree of alkoxylation corresponding to the ratio of the amounts of the substances ethylene oxide and/or propylen oxide and substrate, with which the addition reaction is carried out. $C_{12/18}$ fatty acid mono- and -diesters of addition products of ethylene oxide on glycerol are known from DE 2024051 PS as revertive fatting agents for cosmetic preparations.

$C_{8/18}$ alkyl mono- and oligoglycosides, their manufacture and their use is known from prior art. Their preparation can especially be carried out by reaction of glucose or oligosaccharides with primary alcohols having 8 to 18 C atoms. With regard to the glycoside residue both monoglycosides, where a cyclic sugar group is glycosidic bond to the fatty alcohol, and oligomeric glycosides with a degree of oligomerisation until preferably about 8, are suitable. The degree of oligomerization is then a statistical mean value, based on a distribution of homologues which is usual for such products of technical quality.

Zwitterionic surfactants can also be used as emulsifiers. The term zwitterionic surfactants is intended to mean such surface active compounds which in their molecule have at least a quaternary ammonium group and at least one carboxylate and one sulphonate group. Especially suitable zwitterionic surfactants are the so-called betaines such as the N-alkyl-N,N-dimethyl ammonium glycinates, for example the coco alkyldimethyl ammonium glycinate, N-acylaminopropyl-N,N-dimethyl ammonium glycinate, for example the coco acylaminopropyl dimethyl ammonium glycinate, and 2-alkyl-3-carboxylmethylhydroxyethyl imidazoline with in each case 8 to 18 C atoms in the alkyl or acyl-groups, as well as the coco acylaminoethyl hydroxyethylcarboxymethyl glycinate. Especially preferred is that under the CTFA term cocamidopropyl betaine known fatty acid amide derivative. Also suitable emulsifiers are ampholytic surfactants. Ampholytic surfactants are such surface active compounds which in addition to a $C_{8/18}$ alkyl or acyl group in the molecule at least contain a free amino group and at least one —COOH or —SO$_3$H group and which can form inner salts. Examples of suitable ampholytic surfactants are N-alkyl glycines, N-alkyl propionic acids, N-alkyl aminobutyric acids, N-alkyl iminodipropionic acids, N-hydroxyethyl-N-alkylamidopropyl glycines, N-alkyltaurines, N-alkylsarcosines, 2-alkylaminopropionic acids and alkylamino acetic acids with in each case about 8 to 18 C atoms in the alkyl group. Especially preferable ampholytic surfactants are the N-coco alkylamino propionate, the coco acylamino ethylaminopropionate and the $C_{12/18}$ acylsarcosine. In addition to the ampholytic, also quaternary emulsifiers can be used, of which ester salts of the type of esterquats, preferably methylquaternised di-fatty acid triethanolamine ester salts, are especially preferable.

As hyperfatting agents substances such as for example lanolin and lecithin as well as polyethoxylated or acylated lanolin and lecithin derivatives, polyol fatty acid esters, monoglycerides and fatty acid alkanolamides can be used, whereby the last mentioned at the same time act as foam stabilisers.

As exemplary pearl gloss waxes the following should be mentioned: Alkylene glycolester, especially ethyleneglycol distearate; fatty acid alkanolamides, especially coco fatty acid diethanolamide; partial glycerides, especially stearic acid monoglyceride; esters of polyvalent, possibly hydroxysubstituted carboxylic acids with fatty alcohols with 6 to 22 carbon atoms, especially long chain esters of tartaric acid; fat substances, such as for example fatty alcohols, fatty ketones, fatty aldehydes, fatty ethers and fatty carbonates, wherin the sum of carbon atoms is at least 24, especially lauron and distearyl ethers; fatty acids such as stearic acid, hydroxystearic acid or behenic acid, ring opening products of olefin epoxides with 12 to 22 carbon atoms with fatty alcohols with 12 to 22 carbon atoms and/or polyols with 2 to 15 carbon atoms and 2 to 10 hydroxyl groups as well as their mixtures.

As consistency givers preferably use is made of fatty alcohols or hydroxy fatty alcohols with 12 to 22 and preferably 16 to 18 carbon atoms and additionally partial glycerides, fatty acids or hydroxy fatty acids. A combination of these substances with alkyl oligoglucosides and/or fatty acid-N-methyl glucamides with the same chain length and/or polyglycerol-poly-12-hydroxy stearates.

Suitable thickening agents are for example types of aerosil (hydrophilic silicic acids), polysaccharides, especially xanthan gum, guar-guar, agar-agar, alginates and tyloses, carboxymethyl celluloses and hydroxyethyl celluloses, as well as higher molecular polyethylenglycol mono- and diesters of fatty acids, polyacrylates, (e.g. Carbopols® from Goodrich or Synthalenes® from Sigma), polyacrylamides, polyvinyl alcohol and polyvinyl pyrrolidone, surfactants such as for example ethoxylated fatty acid glycerides, ester of fatty acids with polyols such as for example pentaerythrite or trimethylolpropane, fatty alcohol ethoxytates with narrow distribution of homologous or alkyl oligoglucosides as well as elektrolytes such as sodium chloride and ammonium chloride.

Suitable cationic polymers are for example cationic cellulose derivatives, such as e.g. a quaternized hydroxyethyl cellulose, which is available under the name of Polymer JR 400® from Amerchol, cationic starch, copolymers of diallyl ammonium salts and acrylamides, quaternized vinylpyrrolidone/vinylimidazol polymers, such as e.g. Luviquat® (BASF), condensation products of polyglycols and amines, quaternized collagen polypeptides, such as for example lauryl dimonium hydroxypropyl hydrolyzed collagen (Lamequate®/Grünau), quaternized wheat polypeptides, polyethyleneimine, cationic silicone polymers, such as e.g. amidomethicones, copolymers of adipic acid and dimethylamino hydroxypropyl diethylenetriamine (Cartaretine®/Sandoz), copolymers of acrylic acid with dimethyl diallylammonium chloride (Merquate® 550/Chemviron), polyamino polyamides, such as e.g. described in FR 2252840 A, as well as their cross-linked water soluble polymers, cationic chitin derivatives such as for example quaternized chitosane, possibly micro crystalline distributed, condensation products of dihalogen alkyls, such as e.g. dibromobutane with bisdialkylamines, such as e.g. bis-dimethylamino-1,3-propane, cationic guar-gum, such as e.g. Jaguar® CBS, Jaguar® C-17, Jaguar® C-16 from Celanese, quatemised ammonium salt polymers, such as e.g. Mirapol® A-15, Mirapol® AD-1, Mirapol® AZ-1 from Miranol.

As exemplary anionic, zwitterionic, amphoteric and non-ionic polymers the following can be used: Vinyl acetate/crotonic acid copolymers, vinyl pyrrolidone/vinyl acrylate copolymers, vinyl acetate/butyl maleate/isobornyl acrylate copolymers, methyl vinylether/maleic acid anhydride copolymers and their esters, non-cross-linked and with polyols cross-linked polyacrylic acids, acrylamido propyltrimethyl ammonium chloride/acrylate copolymers, octylacrylamide/methyl methacrylate/tert.-butylaminoethyl methacrylate/2-hydroxypropyl methacrylate copolymers, polyvinylpyrrolidone, vinylpyrrolidone/vinylacetate copolymers, vinylpyrrolidon/dimethylamino ethylmethacrylate/vinyl caprolactam terpolymers as well as possibly derivatized cellulose ethers and silicones.

Suitable silicon compounds are for example dimethyl polysiloxane, methylphenyl polysiloxane, cyclic silicones as well as amino, fatty acid, alcohol, polyether, epoxy, fluorine, glykoside and/or alkyl modified silicon compounds, which at room temperatur can be in the liquid as well as in the resin state. Further suitable are simethicones, which are mixtures of dimethicones with an average chain length of 200 to 300 dimethyl siloxane units and hydrogenated silicates. A detailed survey of suitable volatile silicones can also be found in Todd et al., *Cosm. Toil.* 19, 27 (1976).

Typical exemplary fats are glycerides, and as waxes natural waxes among others, can be used, such as e.g. candelilia wax, carnauba wax, Japan wax, espartogras wax, cork wax, guaruma wax, rice seed oil wax, sugar cane wax, ouricury wax, montan wax, beeswax, schellak wax, spermaceti, lanolin (wool wax), burzel fat, ceresin, ozokerit (terrestrial wax), petrolatum, paraffin waxes, micro waxes; chemically modified waxes (hard waxes), such as e.g. montanester waxes, sasot waxes, hydrogenated yoyoba waxes as well as synthetic waxes, such as e.g. polyalkylene waxes and polyethylene glycol waxes.

As stabilizers metal salts of fatty acids, such as e.g. magnesium, aluminium and/or zinc stearate or ricinoleate can be used.

As biogenic active substances should be understood for example tocopherol, tocopherol acetate, tocopherol palmitate, ascorbic acid, desoxy ribonucleic acid, retinol, bisabolol, allantoin, phytantriol, panthenol, AHA acids, aminoacids, ceramides, pseudoceramides, essential oils, extracts of plants and vitamin complexes.

As deo active agents e.g. antiperspirants such as aluminium chlorohydrate come into question. This agent is in the form of colourless, hygroscopic crystals, which easily melt in air, and is obtained through evaporation of solutions of aluminium chloride in water. Aluminium chlorohydrate is used for manufacturing of perspiration inhibiting and deodorising preparations and has probably its effect through the partial closure of the perspiratory gland by means of precipitation of proteins and/or polysaccharides [see *J. Soc. Cosm. Chem.* 24 281 (1973)]. Under the trade name Locron® of Hoechst AG, Frankfurt/FRG, an aluminium chlorohydrate is for example on the market, which corresponds to the formula $[Al_2(OH)_5Cl]\cdot 2.5\ H_2O$, and use of this is especially preferred (see *J. Pharm. Pharmacol.* 26 531 (1975)]. In addition to the chlorohydrates also aluminium hydroxylactates as well as acid aluminium/zirconium salts can be used. As further deo active agents esterase inhibitors can be added. These are preferably trialkyl citrates such as trimethyl citrate, tripropyl citrate, triisopropyl citrate, tributyl citrate and especially triethyl citrate (Hydagen® CAT, Henkel KGaA, Dusseldorf/FRG). The substances inhibit the enzyme activity and thereby reduce the formation of odours. Probably the free acid is thereby set free through the cleavage of the citric acid ester, and this acid lowers the pH value of the skin so much that the enzymes thereby are inhibited. Further substances which can be used as estersase inhibitors are sterol sulphates or phosphates, such as for example lanosterol, cholesterol, campesterol, stigmasterol and sitosterol sulphate or phosphate, Dicarboxylic acids and their esters, such as for example glutaric acid, glutaric acid monoethylester, glutaric acid diethylester, adipic acid, adipic acid monoethylester, adipic acid diethylester, malonic acid and malonic acid diethylester, hydroxycarboxylic acids and their esters, such as for example citric acid, malic acid, tartaric acid or tartaric acid diethylester. Antibacterial active substances, which influence the germ flora and kill sweat destroying bacterias or inhibit their growth, can also be contained in the pin preparations. Examples of this are chitosan, phenoxyethanol and chlorohexidin gluconate. Also 5-chloro-2-(2,4-dichlorophen-oxy)-phenol has shown to have an especially good effect, and this product is marketed under the trade name Irgasan® by Ciba-Geigy, Basel/CH.

As anti dandruff agents climbazol, octopirox and zinc pyrethion can be used. Useable film formation agents are for example chitosan, microcrystalline chitosan, quaternary chitosan, polyvinylpyrrolidon, vinylpyrrolidon/vinylacetate copolymers, polymers of the acrylic acids, quaternary derivatives of cellulose, collagen, hyaluronic acid or its salts and similar compounds. As swelling agents for aqueous phases montmorillonite, clay mineral substances, pemulen, as well as alkyl modified Carbopol types (Goodrich) can be used. Further suitable polymers or swelling agents can be found in the survey of R. Lochhead in *Cosm. Toil.* 108, 95 (1993).

In addition to the primary light protection substances also secondary light protection substances of the antioxidant type find use, which interrupt the photochemichal reaction chain, which is initiated when UV radiation penetrates the skin. Typical examples of such are amino acids (e.g. glycin, histidin, tyrosin, tryptophan) and their derivatives, imidazoles (e.g. urocaninic acid) and their derivatives, peptides such as D,L-camosine, D-camosine, L-camosine and their derivatives (e.g. anserine), carotinoides, carotine (e.g. α-carotin, β-carotin, lycopin) and their derivatives, chlorogenic acid and its derivatives, liponic acid and its derivatives (e.g. dihydroliponic acid), aurothioglucose, propylthiouracil and other thiols (e.g. thioredoxin, glutathion, cystein, cystin, cystamine and their glycosyl, n-acetyl, methyl, ethyl, propyl, amyl, butyl and lauryl, palmitoyl, oleyl, γ-linoleyl, cholesteryl and glyceryl esters) as well as their salts, dilauryl thiodipropionate, distearyl thiodipropionate, thiodipropionic acid and their derivatives (esters, ethers, peptides, lipides, nucleotides, nucleosides and salts) as well as sulfoximine compounds (e.g. buthionin sulfoximines, homocystein sulfoximines, butionin sulfones, penta-, hexa-, hepta-thionin sufoximine) in very small compatible doses (e.g. pmol to μmol/kg), further (metal) chelating agents (e.g. α-hydroxy fatty acids, palmitic acid, phytinic acid, lactoferrine), α-hydroxy acids (e.g. citric acid, lactic acid, malic acid), humin acid, gallic acid, gallic extracts, bilirubin, bifiverdin, EDTA, EGTA and their derivatives, unsaturated fatty acids and their derivatives (e.g. γ-linolenic acid, linolic acid, oleic acid), folic acid and their derivatives, ubichinon and ubichinol and their derivatives, vitamin C and derivatives (e.g. ascorbyl palmitate, Mg-ascorbyl phosphate, ascorbyl acetate), tocopheroles and derivatives (e.g. vitamin E acetate), vitamin A and derivatives (vitamin A patmitate) as well as koniferyl benzoate of benzoe resin, rutinic acid and their derivatives, α-glycosylrutin, ferula acid, furfuryliden glucitol, carnosine, butylhydroxy toluene, butylhydroxy anisol, nordihydro guajak resin acid, nordihydro guajaret acid, trihydroxy butyrophenon, uric acid and their derivatives, mannose and its derivatives, super oxide dismutase, zinc and its derivatives (e.g. ZnO, $ZnSO_4$), selen and its derivatives (e.g. selen-methionin), stilbenes and their derivatives (e.g. stilben oxide, trans-stilben oxide) and the derivatives suitable according to the invention (salts, esters, ethers, sugars, nucleotides, nucleosides, peptides and lipids) of these mentioned active substances.

For improvement of the flow properties further hydrotropes, such as for example ethanol, isopropyl alcohol, or polyols can be used. Polyols which in this case can be used preferably have 2 to 15 carbon atoms and at least two hydroxyl groups. The polyols can further contain additional functional groups, especially amino groups, or be modified with nitrogen. Typical examples are:

Glycerol;

alkylen glycols, such as for example ethylene glycol, diethylene glycol, propylene glycol, butylene glycol, hexylene glycol as well as polyethylen glycols with an average molecular weight from 100 to 1000 Daltons;

oligoglycerol mixtures of technical quality with a self-condensation degree of 1.5 to 10, such as e.g. technical quality diglycerol mixtures with a diglycerol content of 40 to 50% by weight;

menthol compounds, such as especially trimethylol ethane, trimethylol propane, trimethylol butane, pentaerythrite and dipentaerythrite;

low alkyl glucosides, especially such with 1 to 8 carbons in the alkyl residue, such as for example methyl and butyl glucoside;

sugar alcohols with 5 to 12 carbon atoms, such as for example sorbitol or mannit;

sugars with 5 to 12 carbon atoms, such as for example glucose or saccharose;

aminosugars, such as for example glucamine;

dialcoholamines, such as diethanolamine or 2-amino-1,3-propanediol.

As preservatives for example phenoxyethanol, formaldehyde solution, parabene, pentanediol or sorbic acid as well as those mentioned in enclosure 6, parts A and B of the cosmetic regulation, are further classes of substances. As insect repellents N,N-diethyl-m-toluamide, 1,2-pentanediol or insect repellent 3535 come into question, as self tanning agent dihydroxyaceton is suited.

As perfume oils mixtures of natural and synthetic scent substances should be mentioned. Natural scent substances are extracts of flowers (lilies, lavendel, roses, jasmin, neroli, ylang-ylang), stems and blades (geranium, patchouli, petitgrain), fruits (anis, coriander, caraway, juniper), fruit shells (bergamot, lemon, orange), roots (macis, angelica, celery, kardamon, costus, iris, calmus), wood (stone pine, sandel, guajac, cedar, rosewood), herbs and grass (tarragon, lemongrass, sage, thyme), needles and twigs (spruce, fir, pine, traipsed), resins and balsams (galbanum, elemi, benzoe, myrrh, olibanum, opoponax). Raw materials from animals are also possible, such as for example zibet and castoreum. Typical synthetic odour compounds are products from types of esters, ethers, aldehydes, ketones, alcohols and hydrocarbons. Odour compounds from types of esters are e.g. benzyl acetate, phenoxyethyl isobutyrate, p-tert.-butylcyclohexyl acetate, linalyl acetate, dimethylbenzyl-carbinyl acetate, phenylethyl acetate, linalyl benzoate, benzyl formate, ethylmethylphenyl glycinate, allylcyclohexyl propionate, styrallyl propionate and benzyl salicylate. Benzylethyl ether belongs for example to the ethers, to the aldehydes e.g. the linear alkanales with 8 to 18 carbon atoms, citral, citronellal, citronellyl oxyacetaldehyde, cyclamen aldehyde, hydroxy citronellal, lilial and bourgeonal, to the ketones e.g. the ionones, -isomethyl ionon and methylcedryl ketone, to the alcohols anethol, citronellol, eugenol, isoeugenol, geraniol, linalool, phenylethyl alcohol and terpineol; to the hydrocarbons mainly the terpenes and balsams belong. However, mixtures of different odour substances are preferred, which together give a pleasant smell. Also etheral oils with low volatility, which often are used as aroma components, are suited as perfume oils, e.g. sage oil, chamomile oil, carnation oil, melissa oil, mint oil, cinnamon leaf oil, limeflower oil, juniper berry oil, vetiver oil, oliban oil, galbanum oil, labolanum oil and lavandin oil. Preferably used are bergamot oil, dihydromyrcenol, lilial, lyral, citronellol, phenylethyl alcohol, α-hexylcinnamon aldehyde, geraniol, benzylaceton, cyclamen aldehyde, linalool, boisambrene forte, ambroxane, indol, hedione, sandelice, lemon oil, mandarin oil, orangenoil, allylamyl glycolate, cyclovertal, lavandine oil, muskateller sage oil, β-damascone, geranium oil bourbon, cyclohexyl salicylate, vertofix coeur, iso-E-super, fixolide NP, evemyl, iraidein gamma, phenylacetic acid, geranyl acetate, benzyl acetate, rose oxide, romillate, irotyl and floramate, alone or in mixtures.

As colouring agents such substances which are suited and approved for cosmetic purposes can be used, such as for example those mentioned in the publication "*Kosmetische Färbemittel*" (cosmetic dyes) of the "*Farbstoffkommission der Deutschen Forschungsgemeinschaft*", published by Verlag Chemie, Weinheim, 1984, p. 81–106. These dyes are generally used in concentrations from 0.001 to 0.1% by weight, based on the whole mixture.

Typical examples of germ inhibiting substances are preservatives with specific effects against gram-positive bacteria, such as 2,4,4'-trichloro-2'-hydroxy diphenylether, chlorohexidin (1,6-di-(4-chlorophenyl-biguanido-hexan) or TCC (3,4,4'-trichlorocarbanilide). Many scent substances and etheral oils also have antimicrobial properties. Typical examples are the active agents eugenol, menthol and thymol in carnation, mint and thyme oil. An interesting natural deo substance is the terpene alcohol farnesol (3,7,11-trimethyl-2,6,10-dodecatrien-1-ol), which is present in lime flower oil and has a smell of lilies of the valley. Also glycerol monolaurate have been used as bacteriostaticum. Normally the content of the further germ inhibiting agent is about 0.1 to 2% by weight—based on the solids content of the preparations.

The cumulative contents of the auxiliary and additional agents can be 1 to 50, preferably 5 to 40% by weight, based on the agents. The manufacture of the agents can take place by common cold or hot processes; preferably the work is carried out according to the phase inversion temperature method.

EXAMPLES

The photosensitivity of different UV-A filters in mixture with different oil components was assessed according to the method published by the Merck company on the occasion of the APV seminar from Sep. 17 to 18, 1997 in Fulda. The results are summarized in table 1. For determination of the oil solubility the concentration of saturation was determined for different UV light protection factors in different cosmetic oils in the presence of and in absence of 0.5% by weight of β-(1,3) glucan. The examples 1 to 6 are according to the invention, the examples V1 and V2 are for comparison.

TABLE 1

Photosensitivity

| Composition/performance | 1 | 2 | 3 | 4 | 5 | 6 | V1 | V2 |
|---|---|---|---|---|---|---|---|---|
| Octocrylene | 1.0 | — | — | — | — | — | 1.0 | — |
| Benzophenone-3 | — | 1.0 | — | — | — | — | — | 1.0 |
| Isoamyl p-methoxy cinnamate | — | — | 1.0 | — | — | — | — | — |
| Octyl methoxy cinnamate | — | — | — | 1.0 | — | — | — | — |
| Octyl triazone | — | — | — | — | 1.0 | — | — | — |
| 4-tert.-butyl-methoxy dibenzoylmethane | — | — | — | — | — | 1.0 | — | — |
| Betaglucan* | 0.5 | 0.5 | 0.5 | 0.5 | 0.5 | 0.5 | — | — |
| Coco glycerides | 8.5 | 8.5 | — | — | — | — | 9.0 | 9.0 |
| Dicapryl ether | — | — | 8.5 | 8.5 | — | — | — | — |
| Paraffine oil | — | — | — | — | 8.5 | 8.5 | — | — |
| Water | | | | ad 100 | | | | |
| Photosensitivity (% rel.) | 100 | 100 | 100 | 99 | 99 | 98 | 93 | 92 |
| Oil solubility (% by weight) | 40 | 35 | 42 | 45 | 47 | 45 | 35 | 31 |

*Highcareen ® GS (Henkel KGaA Düsseldorf)

The examples show that in the presence of β-(1,3) glucans both the photosensitivity of the light protection factors as also their solubility in cosmetic oils are significantly improved. The following table 2 contains a range of formulation examples.

TABLE 2

Sun protecting agents (water, preservatives, ad 100% by weight)

| Composition (INCI) | 1 | 2 | 3 | 4 | 5 | 6 | 7 | 8 | 9 | 10 |
|---|---|---|---|---|---|---|---|---|---|---|
| Dehymuls ® PGPH<br>Polyglyceryl-2 dipolyhydroxy stearate | 2.0 | 3.0 | — | 5.0 | — | — | — | — | — | — |
| Lamaform ® TGI<br>Polyglyceryl-3-diisostearate | 4.0 | 1.0 | — | — | — | — | — | — | — | — |
| Ambil ® EM 90<br>Cetyl dimethicone copolyol | — | — | 3.0 | — | — | — | — | — | — | — |
| Emulgade ® PL 68/50<br>Cetearyl glycoside (and) cetearyl alcohol | — | — | — | — | 4.0 | — | — | — | 3.0 | — |
| Eumulgin ® B2<br>Ceteareth-20 | — | — | — | — | — | — | — | 2.0 | — | — |
| Tegocare ® PS<br>Polyglyceryl-3-methylglucose distearate | — | — | — | — | — | — | 4.0 | — | — | — |
| Eumulgin ® VL 75<br>Polyglyceryl-2-dipolyhydroxy stearate (and) lauryl glucoside (and) glycerol | — | — | — | — | — | 3.5 | — | — | 2.5 | — |
| Beesvax | 3.0 | 2.0 | 5.0 | 2.0 | — | — | — | — | — | — |
| Cutina ® GMS<br>Glyceryl stearate | — | — | — | — | — | 2.0 | 4.0 | — | — | 4.0 |
| Lanette ® O<br>Cetearyl alcohol | — | — | 2.0 | — | 2.0 | 4.0 | 2.0 | 4.0 | 4.0 | 1.0 |
| Antaron ® V 216<br>PVP/hexadecene copolymer | — | — | — | — | — | 3.0 | — | — | — | 2.0 |
| Myritol ® 331<br>Coco glycerides | 5.0 | — | 10.0 | — | 8.0 | 6.0 | 6.0 | — | 5.0 | 5.0 |
| Finsolv ® TN<br>C12/15 Alkyl benzoate | — | 6.0 | — | 2.0 | — | — | 3.0 | — | — | 2.0 |
| Cetiol ® J 600<br>Oleyl erucate | 7.0 | 4.0 | 3.0 | 5.0 | 4.0 | 3.0 | 3.0 | — | 5.0 | 4.0 |
| Cetiol ® OE<br>Dicapryl ether | 3.0 | — | 6.0 | 8.0 | 6.0 | 1.0 | 4.0 | 3.0 | 4.0 | 6.0 |
| Mineral oil | — | 4.0 | — | 4.0 | — | 2.0 | — | 1.0 | — | — |
| Cetiole ® PGL<br>Hexadecanol (and) hexyldecyl laurate | — | 7.0 | 3.0 | 7.0 | 4.0 | — | — | — | 1.0 | — |
| Panthenol/bisabolol | 1.2 | 1.2 | 1.2 | 1.2 | 1.2 | 1.2 | 1.2 | 1.2 | 1.2 | 1.2 |
| Highcareen ® GS<br>Betaglucan | 1.0 | 1.0 | 1.0 | 1.0 | 1.0 | 1.0 | 1.0 | 1.0 | 1.0 | 1.0 |
| Copherol ® F 1300 Tocopherol/tocopheryl acetate | 0.5 | 1.0 | 1.0 | 2.0 | 1.0 | 1.0 | 1.0 | 2.0 | 0.5 | 2.0 |
| Neo Heliopan ® Hydro<br>Sodium phenylbenzimidazole sulfonate | 3.0 | — | — | 3.0 | — | — | 2.0 | — | 2.0 | — |
| Neo Heliopan ® 303<br>Octocrylene | — | 5.0 | — | — | — | 4.0 | 5.0 | — | — | 10.0 |
| Neo Heliopan ® BB<br>Benzophenone-3 | 1.5 | — | — | 2.0 | 1.5 | — | — | — | 2.0 | — |
| Neo Heliopan ® E 1000<br>Isoamyl p-methoxy cinnamate | 5.0 | — | 4.0 | — | 2.0 | 2.0 | 4.0 | 10.0 | — | — |

TABLE 2-continued

Sun protecting agents (water, preservatives, ad 100% by weight)

| Composition (INCI) | 1 | 2 | 3 | 4 | 5 | 6 | 7 | 8 | 9 | 10 |
|---|---|---|---|---|---|---|---|---|---|---|
| Neo Heliopan ® AV<br>Octyl methoxy cinnamate | 4.0 | — | 4.0 | 3.0 | 2.0 | 3.0 | 4.0 | — | 10.0 | 2.0 |
| Uvinul ® T 150<br>Octyl triazone | 2.0 | 4.0 | 3.0 | 1.0 | 1.0 | 1.0 | 4.0 | 3.0 | 3.0 | 3.0 |
| Zinc oxide | — | — | — | — | 4.0 | — | — | — | — | 5.0 |
| Titanium dioxide | — | 2.0 | 2.0 | — | — | — | — | 5.0 | — | — |
| Glycerol (86% by weight) | 5.0 | 5.0 | 5.0 | 5.0 | 5.0 | 5.0 | 5.0 | 5.0 | 5.0 | 5.0 |

(1) W/O sun protecting cream, (2–4) W/O sun protecting lotion, (5, 8, 10) O/W sun protecting lotion, (6, 7, 9) O/W sun protecting cream

What is claimed is:

1. A sun protection composition which contains
   a. water soluble β-(1,3) glucans, substantially free of β-(1,6) linkages, and
   b. UV light protection factors.

2. The composition according to claim 1, which contains glucans, which are obtained based on yeasts of the family Saccharomyces.

3. The composition according to claim 2, which contains glucans which are obtained by contacting glucans with, β(1,3) and β-(1,6) linkages in such a way with β-(1,6) glucanases, that practically all β-(1,6) linkages are loosened.

4. The composition according to claim 1, wherein glucans are used which have previously been treated with glucanases based on *Trichodermia harzianum*.

5. The composition according to claim 1, which contains oil soluble UVB light protection factors, which have been chosen from the group formed by 3-benzylidene camphor or 3-benzylidene norcamphor and derivatives thereof, 4-aminobenzoic acid derivatives, cinnamon acid esters, salicylic acid esters, benzalmalonic acid esters, benzophenon derivatives, triazine derivatives and propane-1,3-diones.

6. The composition according to claim 1, which contains water soluble UVB light protection factors, which have been chosen from the group formed by 2-phenylbenzimidazol-5-sulfonic acid and its alkali, alkaline earth, ammonium, alkyl ammonium, alkanol ammonium and glucammonium salts as well as sulfonic acid derivatives of benzophenones or 3-benzylidene camphor.

7. The composition according to claim 1, which contains UVB light protection factors, which have been chosen from the group formed by 1-(4'-tert.-butylphenyl)-3-(4'methoxyphenyl)-propane-1,3-dion, 4-tert.-butyl-4'-methoxy dibenzoyl methane and 1-phenyl-3-(4'-isopropylphenyl)-propane-1,3-dion.

8. The composition according to claim 1, which contains insoluble UVB light protection factors, which have been chosen from the group formed by fine disperse oxides of zinc, titanium, iron, zirconium, silicon, manganese, aluminum and cerium, as well as fine disperse silicates, barium sulphate and zinc stearate.

9. The composition according to claim 1, which contains
   a. 0.01 to 25% by weight of water soluble β-(1,3) glucans, which are substantially free from β-(1,6) linkages, and
   b. 0.05 to 10% by weight of UV protection factors provided that the stated amounts are supplemented with water as well as possibly other auxiliaries and additional agents up 100% by weight.

10. Method for improving the photo sensitivity and solubility of UV light protection factor in sun protecting agents comprising including water soluble β-(1,3) glucans which are substantially free from β-(1,6) linkages.

* * * * *